United States Patent [19]

Evans

[11] 4,235,820

[45] Nov. 25, 1980

[54] PROCESS FOR DIBENZOCYCLOHEPTENE COMPOUNDS

[75] Inventor: Ben E. Evans, Lansdale, Pa.

[73] Assignee: Merck & Co., Inc., Rahway, N.J.

[21] Appl. No.: 713,306

[22] Filed: Aug. 10, 1976

[51] Int. Cl.$^3$ .................... C07C 5/327; C07C 5/333; C07C 87/28
[52] U.S. Cl. .................... 564/427; 564/99; 568/659; 568/661
[58] Field of Search ............ 260/570.8 TC, 611 F, 260/558.8 TC, 609 R, 556 A, 556 AR, 590 FB; 568/695, 661

[56] References Cited

U.S. PATENT DOCUMENTS 3,546,228   12/1970   Kaiser et al. .................... 260/570.8

OTHER PUBLICATIONS

Gribble et al., "Journal American Chemical Society", vol. 96, pp. 7812-7814 (1974).
Gaylord, "Reduction with Complex Metal Hydrides", pp. 32-33 and 283 (1956).
Bapat et al., "Tetrahedron Letters", No. 5, pp. 15-19 (1960).

*Primary Examiner*—Robert V. Hines
*Attorney, Agent, or Firm*—Thomas E. Arther; Harry E. Westlake, Jr.

[57] ABSTRACT

This invention relates to a process for the preparation of 5H-dibenzo[a,d]cycloheptene compounds and derivatives having aminoalkyl substituents at the 5-position by reducing the corresponding 5-aminoalkyl-5-hydroxy compounds with an alkali metal borohydride in trifluoroacetic acid.

13 Claims, No Drawings

PROCESS FOR DIBENZOCYCLOHEPTENE COMPOUNDS

BACKGROUND OF THE INVENTION

Certain 5H-dibenzo[a,d]cycloheptene compounds having aminoalkyl substituents at the 5-position have been prepared in the past using a 5H-dibenzo[a,d]cycloheptene-5-one compound as starting material using a variety of circuitous routes to introduce the 5-position aminoalkyl side chain without affecting double bonds or other functional substituents susceptible to attack by catalytic hydrogenation. Included are the 10,11-dihydro-5H-dibenzo[a,d]cycloheptenes having other susceptible substituents in the molecule.

A preferred group of such compounds have the following structural formula:

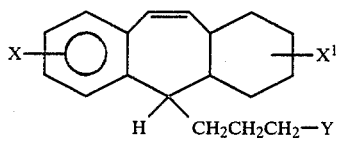

wherein Y is a loweralkoxy substituent or an amino substituent which may be mono- or dialkylated, e.g.,

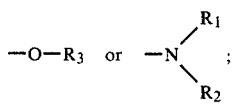

X and $X^1$ are similar or dissimilar and are selected from hydrogen, an alkyl group having up to 6 carbon atoms, an alkenyl group having up to 6 carbon atoms, a perfluoroalkyl group having up to 4 carbon atoms, a phenyl or a substituted phenyl radical, an amino, an alkylamino group having up to 4 carbon atoms, a dialkylamino group having up to 8 carbon atoms, an alkylsulfonylamino group having up to 4 carbon atoms, halogen (fluorine, chlorine, bromine, or iodine), hydroxyl, an alkoxyl group having up to 4 carbon atoms, a perfluoroalkoxyl group having up to 4 carbon atoms, an alkylmercapto group having up to 4 carbon atoms, a perfluoroalkylmercapto group having up to 4 carbon atoms, an alkylsulfonyl group having up to 4 carbon atoms, a perfluoroalkylsulfonyl group having up to 4 carbon atoms, sulfamoyl, an alkylsulfamoyl group having up to 4 carbon atoms, or a dialkylsulfamoyl group having up to 8 carbon atoms; more than one of these substituents may be on each benzenoid ring and the compounds may have substituents on the propyl chain such as lower alkyl radicals, preferably having from 1 to 4 carbon atoms;

$R_1$ and $R_2$ are each either hydrogen, an alkyl of 1–5 carbons (including branched chain alkyl), or cycloalkyl substituents containing 1–5 carbons, for example, N-methyl-5H-dibenzo[a,d]cycloheptene-5-propylamine; and $R_3$ is alkyl of 1–5 carbons.

Certain of these prior art methods are described in U.S. Pat. No. 3,372,196 of Edward L. Engelhardt and in a publication of Engelhardt et al., J. Med. Chem., 11, 326–332 (1968). One such typical method begins with 5H-dibenzo[a,d]cycloheptene-5-one and first converts the ketone to the corresponding 5-hydroxy compound by reduction with borohydride followed by treatment with dry hydrogen chloride to produce the corresponding 5-chloro-5H-dibenzo[a,d]cycloheptene. This compound is then coupled with a Grignard reagent derived from dimethylaminopropyl chloride to produce the desired N,N-dimethyl-5H-dibenzo[a,d]cycloheptene-5-propylamine which is demethylated to the corresponding N-methyl derivative. Another method, disclosed in the above-mentioned patent, to prepare compounds of the type described involves the reaction of a 5H-dibenzo[a,d]cycloheptene-5-one with an alkoxypropyl magnesium halide to produce the corresponding 5-alkoxypropyl-5-hydroxy-5H-dibenzo[a,d]cycloheptene and reducing this compound using hydrogen iodide in acetic anhydride to produce a 5-(3-iodopropyl)-5H-dibenzo[a,d]cycloheptene in low yield. This compound is then reacted with ammonia or a lower alkyl or dialkyl amine to produce the corresponding 5-(3-aminopropyl, 3-alkylaminopropyl, or 3-dialkylaminopropyl)-5H-dibenzo[a,d]cycloheptene. Compounds of this type have tetrabenazine antagonist activity and are useful in the treatment of humans affected by depression as reported in the above-noted J. Med. Chem. article or as disclosed in the above-noted U.S. Pat. No. 3,372,196 of Engelhardt or are useful as intermediates in the preparation of such compounds.

SUMMARY OF THE INVENTION

The present invention relates to a method of reductive dehydroxylation of a 5-(3-aminoalkyl or 3-alkoxyalkyl)-5-hydroxy-5H-dibenzo[a,d]cycloheptene compound having one or more substituents or centers of unsaturation susceptible to catalytic hydrogenation by treatment of said cycloheptene compound with a borohydride compound in trifluoroacetic acid. Thus, in accordance with our invention, a compound of the structure:

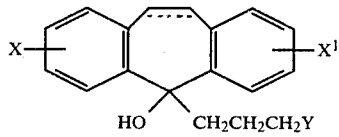

wherein X, $X^1$, and Y are as defined above and the dotted line indicates an optional additional bond which contains at least one catalytically reducible substituent or center of unsaturation, is contacted with a mixture of an alkali metal or tetraalkyl ($C_{1-4}$) ammonium borohydride and trifluoroacetic acid to produce the corresponding compound of the structure:

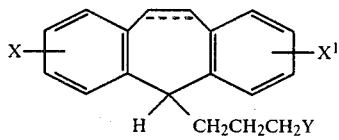

This invention further relates to a novel process of reducing a compound of the structure:

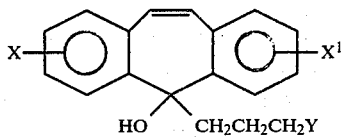

wherein X, X¹, and Y are as defined above by contacting said compound with an alkali metal or ammonium borohydride in the presence of trifluoroacetic acid with resulting production of the corresponding compound of the formula:

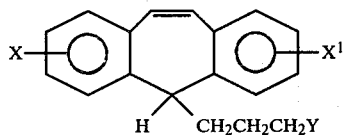

The reaction is carried out at temperatures between 0° C. and 30° C. depending on the specific reaction conditions. A preferred method of operation is to add a mixture of the starting carbinol and a large molar excess of powdered sodium borohydride to trifluoroacetic acid at 0° C. in an inert atmosphere with stirring for a period of from about 15 minutes to 2 hours during which time the temperature is allowed to rise from 0° C. to about 15° C. Following completion of the reaction, the product is recovered after removing the trifluoroacetic acid by evaporation under reduced pressure, followed by dilution of the residue with water, basification, and recovery by filtration or extraction with a solvent for the reduced product.

When the preferred procedure is employed, the described product is obtained in consistently high yields, thus avoiding the circuitous methods employed in the prior art described in part hereinabove.

In a method of producing compounds in accordance with the present invention, i.e., the 5-(3-aminopropyl, 3-alkylaminopropyl, or the 3-dialkylaminopropyl)-5H-dibenzo[a,d]cycloheptenes, the substituted dibenzo[a,d]cycloheptenone starting material is reacted with an appropriate Grignard reagent, for example, a 3-ethoxypropylmagnesium halide, to produce the corresponding 5-(3-ethoxypropyl)-5H-dibenzo[a,d]cyclohepten-5-ol. The carbinol substituent is treated in accordance with the process of the present invention by reduction with an alkali metal borohydride in trifluoroacetic acid to produce the corresponding 5-(3-ethoxypropyl)-substituted 5H-dibenzo[a,d]cycloheptene, followed by treatment with phosphoric acid and P₂O₅ and potassium iodide at an elevated temperature to produce the corresponding 5-(3-iodopropyl) derivative. The iodo compound is readily converted by treatment with a selected alkylamine, for example, methylamine, to produce the corresponding alkylaminopropyl, i.e., N-methylaminopropyl-substituted 5H-dibenzo[a,d]cycloheptene compound.

The process of our invention is described in the following examples. All temperatures are in degrees Celsius.

EXAMPLE 1A

3-Iodo-7-nitro-5H-dibenzo[a,d]cyclohepten-5-one

3-Amino-7-nitro-5H-dibenzo[a,d]cyclohepten-5-one (30 g., 0.113 mole) is dissolved in 270 ml. of warm glacial acetic acid, and the solution cooled to 15° in an ice water bath.

Powdered sodium nitrite (11.4 g., 0.166 mole) is added slowly to 62 ml. of cooled concentrated sulfuric acid. The mixture is warmed gently to effect solution, then re-cooled and added dropwise to the well-stirred acetic acid slurry. The temperature of the mixture is maintained at ca 20°.

On completion of the addition, the thick mass is stirred for 10 minutes, then poured into a vigorously-stirred solution of 27 g. (0.163 mole) of potassium iodide in 135 ml. of water. The mixture is allowed to stand at room temperature overnight, warmed on a steam bath 15 minutes, cooled, and filtered. The crude orange solid, vacuum dried, weighs 34 g. (m.p. 226°–240°) and exhibits substantial starting material by thin layer chromatography.

The solid is pulverized in a mortar, mixed with 160 ml. of concentrated hydrochloric acid and 50 g. of ice, and cooled in an ice bath to 0°.

To the cooled, stirred slurry is added a solution of sodium nitrate (7 g., 0.102 mole) in 32 ml. of water. The mixture is stirred 1.5 hours at 0°, then added to a well-stirred solution of 85 g. (0.51 mole) of potassium iodide in 55 ml. of water. The mixture is warmed on a steam bath for 5 minutes, cooled, treated with sodium bisulfite solution to discharge the iodine color and filtered. The crude solid (m.p. 234°–241°), washed with water and dried in a stream of warm air, weighs 38 g. (89%); 3-iodo-7-nitro-5H-dibenzo[a,d]cyclohepten-5-one.

EXAMPLE 1B

3-Amino-7-iodo-5H-dibenzo[a,d]cyclohepten-5-one

3-Iodo-7-nitro-5H-dibenzo[a,d]cyclohepten-5-one (23.4 g., 0.062 mole) in 140 ml. of glacial acetic acid is heated to 90° and treated with stannous chloride dihydrate (52 g., 0.23 mole), added in portions as the solid. The temperature of the mixture is maintained between 95° and 100° throughout the addition and for 10–15 minutes thereafter. The mixture is then cooled to ca 50° and poured into 1 liter of ice water.

The resulting slurry is filtered and the solid washed several times with water and dried in vacuum. The crude yellow solid is washed with sodium hydroxide solution, filtered, and dried in a stream of warm air. The resulting solid is extracted 5 times with boiling toluene (500 ml.), and the combined extracts are filtered and evaporated to dryness in vacuo. The solid obtained is boiled with 600 ml. of chloroform and the slurry filtered. The filtrate is treated with silica gel, added in portions with tlc assay of the supernatant after each addition (5% ethyl acetate in chloroform on silica gel plates). When the polar baseline spot is nearly absent, the hot slurry is filtered and the brilliant yellow filtrate evaporated in vacuo to give the crude title compound as a yellow-orange solid, m.p. 140°–175°.

EXAMPLE 1C

3-Amino-5-(3-ethoxypropyl)-7-iodo-5H-dibenzo[a,d]cyclohepten-5-ol

In thoroughly dried apparatus, magnesium turnings (2.9 g., 0.119 mole) are covered with dry tetrahydrofuran (10 ml.) and treated with a solution of 3-ethoxypropylbromide (20.0 g., 0.119 mole) in tetrahydrofuran (100 ml.), added dropwise at a rate sufficient to maintain modest reflux. Upon completion of the addition, the mixture is heated at reflux for 15 minutes, then cooled in an ice water bath.

Solid 3-Amino-7-iodo-5H-dibenzo[a,d]cyclohepten-5-one (11.7 g., 0.034 mole) is added in portions directly to the stirred Grignard solution. Following the addition, the mixture is stirred for 5 minutes and poured into 100 ml. of saturated ammonium chloride solution. The layers are separated, and the aqueous layer extracted twice with ether. The ether extracts combined with the organic layer are washed once with water, dried over sodium sulfate, filtered, and evaporated in vacuo to give 19.5 g. of red-brown oil.

Column chromatography on 180 g. of silica gel eluted with chloroform and 5%, 10%, and 20% methanol in chloroform affords a product fraction which is evaporated in vacuo at 60° to give 12.8 g. (87%) of red-brown oil.

EXAMPLE 1D

3-Amino-5-(3-ethoxypropyl)-7-iodo-5H-dibenzo[a,d]cycloheptane

3-Amino-5-(3-ethoxypropyl)-7-iodo-5H-dibenzo[a,d]cyclohepten-5-ol (8.5 g., 0.020 mole) and sodium borohydride (7.2 g., 0.19 mole) are ground together in a mortar and the resulting mass added in portions to 200 ml. of trifluoroacetic acid, cooled in ice, and stirred vigorously under a stream of nitrogen in an efficient fume hood. Upon completion of the addition, the mixture is stirred for 15 minutes, then evaporated in vacuo to a thick mass. Ice water (ca 100 ml.) is added and the mixture stirred for 1 hour.

The suspension is made basic with concentrated sodium hydroxide solution, and extracted three times with ether. The combined ether layers are washed with water, dried over sodium sulfate, filtered, and evaporated in vacuo to give 7.9 g. (97%) of product as an oil.

The Example is repeated using an equivalent amount of lithium, potassium, tetramethyl, or tetraethyl ammonium borohydride in place of the sodium borohydride used in the preceding Example.

EXAMPLE 1E

3-Amino-5-(3-iodopropyl)-7-iodo-5H-dibenzo[a,d]cycloheptene

Phosphorous pentoxide (3.75 g., 0.026 mole) is added to 5.28 ml. of concentrated phosphoric acid (85%) with stirring. The viscous mixture is cooled and added to 7.9 g. (0.019 mole) of 3-amino-5-(3-ethoxypropyl)-7-iodo-5H-dibenzo[a,d]cycloheptene. The thick slurry is stirred and treated with 13.0 g. (0.079 mole) of pulverized potassium iodide. The resulting mass is stirred and heated overnight in a thermostatted oil bath (110°).

The mixture is cooled, cold water added, and the resulting suspension extracted repeatedly with chloroform until all the solid is dissolved. The chloroform layer is washed with dilute aqueous sodium bisulfite, dilute sodium bicarbonate solution, and water, and dried over sodium sulfate. Filtration and vacuum evaporation provides 8.0 g. of dark brown oil.

The oil, in chloroform, is chromatographed on 250 g. of silica gel eluted with chloroform, 2%, 3%, 4%, 5%, 7%, 10%, and 12% methanol in chloroform. The separation provides 4.0 g. (42%) of product and 2.7 g. (34%) recovered starting material.

EXAMPLE 1F

N-Methyl-3-(3-amino-7-iodo-5H-dibenzo[a,d]cyclohepten-5-yl)propylamine hydrochloride A solution of 3-amino-5-(3-iodopropyl)-7-iodo-5H-dibenzo[a,d]cycloheptene (4.0 g., 0.008 mole) in 200 ml. of benzene is saturated with methylamine gas, stoppered, and stirred for 72 hours. The mixture is evaporated in vacuo, taken up in ether, and treated with ethanolic HCl until acidic. The gray solid is separated by filtration and air dried (2.5 g., 71%; m.p. ~200° indef.).

EXAMPLE 1G

N-Methyl-3-(3,7-diiodo-5H-dibenzo[a,d]cyclohepten-5-yl)propylamine hydrochloride N-Methyl-3-(3-amino-7-iodo-5H-dibenzo[a,d]cyclohepten-5-yl)propylamine hydrochloride (0.3 g., 0.68 mmole) slurried in 2 ml. of concentrated hydrochloric acid is stirred in an ice/salt bath and treated with a solution of 0.057 g. (0.83 mmole) of sodium nitrite in 1 ml. of $H_2O$ added dropwise. The mixture is stirred until homogeneous then added slowly to a stirred solution of 0.166 g. (1.0 mmole) of potassium iodide in 1 ml. of water. The slurry is diluted to 5 ml. with water, stirred for 15 minutes at room temperature, and warmed on a steam bath for another 15 minutes.

The suspension is treated with aqueous sodium bisulfite followed by dilute sodium hydroxide until basic, and extracted three times with chloroform (10 ml.). The combined chloroform fractions are washed with water, dried over sodium sulfate, filtered, and concentrated in vacuo to 0.3 g. of orange oil.

The oil, in chloroform, is chromatographed on 18 g. of silica gel, eluted with chloroform/ammonia (chloroform shaken with an equal volume of concentrated aqueous ammonia and separated from the aqueous fraction). The evaporated product fraction is dissolved in ether and treated with ethanolic HCl to afford the homogeneous product as the hydrochloride (0.15 g., 43%; molecular ion of free base measured 514.9599, calc'd for $C_{19}H_{19}I_2N$ 514.9611, error 2.3 ppm).

EXAMPLE 2A

3-Amino-5H-dibenzo[a,d]cyclohepten-5-one

3-Bromo-5H-dibenzo[a,d]cyclohepten-5-one (25 g., 0.088 mole), copper turnings (0.018 mole), cuprous chloride (0.94 g., 0.009 mole), and concentrated aqueous ammonia (50 ml.) are agitated together at 195° in a steel bomb for 24 hours.

The cooled mixture is removed from the vessel, and the large solid mass broken up mechanically and dissolved in warm chloroform (ca 150 ml.). The aqueous residue from the reaction is extracted once with chloroform, and the combined chloroform fractions are washed with water, dried over sodium sulfate, filtered, and evaporated in vacuo to give 18.9 g. of crude yellow solid.

The crude product is ground in a mortar and recrystallized from ethanol (ca 200 ml.). The solid obtained is dissolved in warm chloroform, treated with ca 8 g. of silica gel, filtered, and evaporated in vacuo to give 16 g. of the title compound.

EXAMPLE 2B

3-Amino-5-(3-ethoxypropyl)-5H-dibenzo[a,d]cyclohepten-5-ol

Magnesium turnings (6.2 g., 0.255 mole) covered with dry tetrahydrofuran (30 ml.) in carefully-dried apparatus are treated with a solution of 3-ethoxypropylbromide (42.5 g., 0.255 mole) added dropwise to maintain reflux. After preparation of the Grignard reagent according to standard procedures, the mixture is cooled, and 16 g. (0.072 mole) of 3-amino-5H-dibenzo[a,d]cyclohepten-5-one added in portions over 5 minutes. The reaction is stirred 15 minutes, then poured into 200 ml. of saturated aqueous ammonium chloride. The layers are separated, and the aqueous layer extracted once with ether. The ether layer, combined with the original organic phase, is washed once with water, dried over sodium sulfate, and evaporated in vacuo to give the title compound in essentially quantitative yield.

EXAMPLE 2C

3-Amino-5-(3-ethoxypropyl)-5H-dibenzo[a,d]cycloheptene

3-Amino-5-(3-ethoxypropyl)-5H-dibenzo[a,d]cyclohepten-5-ol (10 g., 0.032 mole) and sodium borohydride (12.3 g., 0.325 mole) are ground together in a mortar. The mixture is added in portions to 250 ml. of trifluoroacetic acid, cooled in ice, and stirred vigorously under a stream of nitrogen in an efficient fume hood. Upon completion of the addition, the mixture is stirred for 15 minutes and the bulk of the trifluoroacetic acid removed under vacuum.

The resulting mass is treated with 600 ml. of ice water, and the aqueous phase separated from the insoluble organic gum by decantation. The organic residue is stirred with chloroform and sodium hydroxide solution until the solid has dissolved, and the chloroform layer is separated, washed with water, dried over sodium sulfate, and evaporated in vacuo to provide the title compound as a brown oil.

EXAMPLE 2D

3-Amino-5-(3-iodopropyl)-5H-dibenzo[a,d]cycloheptene

Phosphorus pentoxide (7.8 g., 0.054 mole) is treated with 7.8 g. of concentrated (85%) phosphoric acid. To the cooled solution is added powdered potassium iodide (40.5 g., 0.244 mole). The suspension is added to 12 g. (0.041 mole) of 3-amino-5-(3-ethoxypropyl)-5H-dibenzo[a,d]cycloheptene and the resulting mass stirred and heated for 3 hours at 110° (oil bath).

The mixture is cooled, treated with dilute sodium hydroxide until slightly basic, and extracted three times with chloroform. The combined chloroform layers are washed once with water, dried over sodium sulfate, and evaporated in vacuo.

The resulting oil is chromatographed on 470 g. of silica gel eluted with chloroform. The title compound is obtained as an oil in 48% yield.

EXAMPLE 2E

N-Cyclopropyl-3-(3-amino-5H-dibenzo[a,d]cyclohepten-5-yl)propylamine hydrochloride 3-Amino-5-(3-iodopropyl)-5H-dibenzo[a,d]cycloheptene (7.2 g., 0.019 mole) is stirred 48 hours at room temperature with 5.5 g. (0.096 mole) of cyclopropylamine. The mixture is evaporated in vacuo. The residue is dissolved in chloroform, extracted with sodium hydroxide, washed with water, dried over sodium sulfate, and evaporated in vacuo. Ether is added to the resulting oil followed by ethanolic HCl (until acidic). The solvent is again removed in vacuo and the residue treated with ether to afford 5.3 g. of the title compound (81%; m.p. indefinite, 160°–200° ↑).

EXAMPLE 2f

N-Cyclopropyl-3-(3-iodo-5H-dibenzo[a,d]cyclohepten-5-yl)propylamine hydrochloride N-Cyclopropyl-3-(3-amino-5H-dibenzo[a,d]cyclohepten-5-yl)propylamine hydrochloride (0.3 g., 0.88 mmole) in 2 ml. of concentrated hydrochloric acid is stirred in an ice/salt bath and diazotized by dropwise addition of a solution of 0.076 g. (1.1 mmole) of sodium nitrite in 1 ml. of water. The mixture is stirred for 10 minutes, then added slowly to a solution of 0.207 g. (1.25 mmole) of potassium iodide in 1 ml. of water. The mixture is stirred for 15 minutes at room temperature and warmed on a steam bath for an additional 10 minutes.

The resulting suspension is treated with dilute sodium hydroxide and sodium bisulfite, then extracted three times with chloroform. The combined chloroform extracts are washed with water, dried over sodium sulfate, and evaporated in vacuo. The residue is dissolved in chloroform, passed through a pad of alumina, and treated with ethanolic HCl.

The solution is evaporated in vacuo and triturated with ether to give 0.25 g. (69%) of the title compound as a pale tan amorphous powder.

EXAMPLE 3A

10,11-Dihydro-3,7-diiodo-5H-dibenzo[a,d]cyclohepten-5-one 10,11-Dihydro-5H-dibenzo[a,d]cyclohepten-5-one (84 g., 0.402 mole), 600 ml. of conc. sulfuric acid, 60 ml. of water, 177 g. (0.567 mole) of silver sulfate, and 178 g. (0.70 mole) of powdered iodine are mixed and stirred mechanically overnight.

The mixture is poured into 2 liters of ice water, stirred with 400 ml. of CHCl₃, and filtered. The solids are washed twice with ca 200 ml. of hot chloroform. The filtrate is separated, and the aqueous fraction extracted twice with ca 200 ml. of chloroform. The combined chloroform fractions are washed once with dilute sodium bisulfite solution and once with water, dried over sodium sulfate, and evaporated in vacuo. The thick mass obtained is washed five times with 200 ml. portions of ether, leaving the product as a solid (63.5 g., 34%). This is recrystallized from 1:1 chloroform/hexane; m.p. 160°–162°.

EXAMPLE 3B

3,7-Diiodo-5H-dibenzo[a,d]cyclohepten-5-one 10,11-Dihydro-3,7-diiodo-5H-dibenzo[a,d]cyclohepten-5-one (54.1 g., 0.118 mole), N-bromosuccinimide (24 g., 0.135 mole), and dibenzoyl peroxide (0.32 g., 0.001 mole) are heated in refluxing carbon tetrachloride (360 ml.) unit the refluxate is colorless. The mixture is filtered warm, and the solid washed once with warm carbon tetrachloride, once with 1 N NaOH, and twice with hot water. Dried in a stream of warm air, the bromide (51.6 g.) melts at 248°–250° (d).

This solid is combined with 635 ml. of benzene and 315 ml. of triethylamine and heated at reflux for 18 hours. The mixture is cooled on ice and filtered. The solid is washed once with dilute hydrochloric acid and once with water, re-filtered, and dried in vacuo at 60° overnight; 40.3 g. (75%), recrystallized from toluene, m.p. 260.5°–263°.

EXAMPLE 3C 3,7-Diiodo-5-(3-N,N-dimethylaminopropyl)-5H-dibenzo[a,d]cyclohepten-5-ol 3-(N,N-Dimethylamino)-propylmagnesium chloride (11 ml. of 3 M solution in tetrahydrofuran) is diluted with tetrahydrofuran (10 ml.) and stirred in an ice bath. 3,7-Diiodo-5H-dibenzo[a,d]cyclohepten-5-one (8.5 g., 0.019 mole) is added directly, in portions, to the Grignard solution. Upon completion of the addition, the solution is stirred for one hour, concentrated in vacuo, and treated with 5 ml. of water. The resulting gummy mass is extracted six times with boiling methylene chloride, and the combined methylene chloride fractions are washed once with water, dried over sodium sulfate, and evaporated in vacuo. The sticky residue is washed twice with water, filtered, and dried in a stream of warm air. The pale yellow solid (8.2 g., 84%) melts at 218°–223°.

EXAMPLE 3D

N,N-Dimethyl-3-(3,7-diiodo-5H-dibenzo[a,d]cyclohepten-5-yl)propylamine 3,7-Diiodo-5-(3-N,N-dimethylaminopropyl)-5H-dibenzo[a,d]cyclohepten-5-ol (8.1 g., 0.015 mole) and sodium borohydride (5.4 g., 0.14 mole) are mixed well, and the mixture added in portions to 200 ml. of trifluoroacetic acid cooled in an ice bath and stirred vigorously under a stream of nitrogen in an efficient fume hood.

Following completion of the addition, the mixture is stirred for 15 minutes, and the bulk of the trifluoroacetic acid is removed under vacuum. Ice water (500 ml.) is added to the residue, and the aqueous layer decanted from the sticky organic product. The latter is dissolved in ether, extracted three times with 1 N NaOH, washed with water, dried over sodium sulfate, and evaporated in vacuo to give 7.3 g. (93%) of pale yellow solid.

EXAMPLE 3E

N-Methyl-3-(3,7-diiodo-5H-dibenzo[a,d]cyclohepten-5-yl)propylamine hydrochloride N,N-Dimethyl-3-(3,7-diiodo-5H-dibenzo[a,d]cyclohepten-5-yl)propylamine (7.3 g., 0.014 mole) in 30 ml. of benzene is added dropwise to 1.6 g. (0.015 mole) of vinyl chloroformate in 25 ml. of benzene stirred in an ice bath. Upon completion of the addition, the mixture is stirred at 30° for 15 minutes, and at 50°, another 60 minutes. The clear, pale yellow supernatant is decanted from the residual gum, filtered, and evaporated in vacuo to a yellow oil.

The oil is dissolved in 30 ml. of methylene chloride, and dry HCl gas is bubbled into the stirred solution for 15 minutes. The solution is stirred an additional 2 hours at room temperature. The solvent is then removed in vacuo, 17 ml. of absolute ethanol is added, and the resulting solution refluxed gently on the steam bath for 10 minutes. Water (2 ml.) is added and refluxing continued for another 5 minutes. The mixture is set aside, and soon deposits beautiful white crystals which are separated by filtration and dried in vacuo at 60° overnight (m.p. 279.5°–281.5°).

EXAMPLE 4A

3-Iodo-5H-dibenzo[a,d]cyclohepten-5-one 3-amino-5H-dibenzo[a,d]cyclohepten-5-one (50 g., 0.226 mole) is slurried in 150 ml. of concentrated hydrochloric acid. Ice (150 ml.) is added, and the stirred mixture cooled in an ice bath and diazotized by dropwise addition of sodium nitrite solution (17 g., 0.248 mole in 80 ml. of water) over 45 minutes. The temperature is held below 5° throughout the addition. The mixture is stirred for an additional 15 minutes and poured slowly into a stirred solution of 160 g. (1 mole) of potassium iodide in 100 ml. of water. The mixture is stirred at room temperature for 1 hour, then stored overnight in the refrigerator.

The resulting slurry is filtered and the filtrate is extracted once with chloroform. The solids are extracted several times with hot chlorform, and the combined chloroform fractions washed with dilute sodium bisulfite and with water, and dried over sodium sulfate. Residual solid from the chloroform extraction is discarded.

The chloroform solution is combined with 100 g. of silica gel, evaporated in vacuo, then stirred with 1:1 chloroform/hexane and added to a column of 1 kg. of silica gel. The column is packed and eluted with 1:1 chlorform/hexane. The product fraction, which is eluted after ca 3.5 liters of fore-run, is evaporated in vacuo to give the title compound (39.7 g., 53%) as a white solid, m.p.

97.5°–99°.

EXAMPLE 4B

3-Iodo-5-(3-N,N-dimethylaminopropyl)-5H-dibenzo[a,d]cyclohepten-5-ol

3-Iodo-5H-dibenzo[a,d]cyclohepten-5-one (20 g., 0.060 mole) in 100 ml. of dry THF is cooled in an ice bath and treated with 45 ml. of 2.5 M 3-(N,N-dimethylamino)-propylmagnesium chloride added dropwise over 15 minutes. The mixture is stirred another 15 minutes at room temperature, then concentrated in vacuo. Toluene (100 ml.) is added to the residue followed by 35 ml. of water (added dropwise with stirring). The resulting mass is extracted 6 times with boiling toluene.

The combined toluene fractions are washed once with water, dried over sodium sulfate, and evaporated in vacuo to give the title compound (25.2 g., ca 100%) as a pale yellow solid, m.p. 137.5°–139.5°.

EXAMPLE 4C

N,N-Dimethyl-3-(3-iodo-5H-dibenzo[a,d]cyclohepten-5-yl)propylamine

3-Iodo-5-(3-N,N-dimethylaminopropyl)-5H-dibenzo[a,d]cyclohepten-5-ol (10 g., 0.024 mole) is mixed thoroughly with 9.1 g. (0.24 mole) of sodium borohydride. The mixture is added in portions to 200 ml. of trifluoroacetic acid and stirred vigorously in an ice bath. The addition is carried out in a well ventilated hood, and a modest stream of nitrogen is passed over the mixture throughout the addition process.

The mixture is then stirred for ½ hour, filtered rapidly through cheesecloth, and evaporated in vacuo. The residue is treated with 100 ml. of ice water, made basic by addition of concentrated sodium hydroxide, and extracted three times with ether. The combined ether extracts are washed with water, dried over sodium sulfate, and evaporated in vacuo to give the title compound (9.4 g., 98%) as a pale orange oil.

EXAMPLE 4D

N-Methyl-3-(3-iodo-5H-dibenzo[a,d]cyclohepten-5-yl)propylamine hydrogen oxalate

N,N-dimethyl-3-(3-iodo-5H-dibenzo[a,d]cyclohepten-5-yl)propylamine (9.4 g., 0.023 mole) is dissolved in 35 ml. of benzene and the solution added dropwise to 30 ml. of benzene containing 2.71 g. (0.026 mole) of vinyl chloroformate stirred in an ice bath. Upon completion of the addition, the mixture is stirred for 5 minutes at ca 30°, and for ½ hour at 50°–60°. The liquid phase is decanted through cheesecloth and concentrated in vacuo. The resulting residue is dissolved in 40 ml. of methylene chloride and HCl gas is passed through the stirred solution for 15 minutes. The mixture is stirred at room temperature for another 2 hours, evaporated in vacuo, and redissolved in ethanol. The ethanol solution is evaporated and the residue redissolved in fresh ethanol and allowed to stand 72 hours in the refrigerator.

The solution is evaporated, treated with dilute sodium hydroxide, and extracted three times with chloroform. The combined chloroform layers, washed once with water, dried over sodium sulfate, and evaporated in vacuo, provide 8.3 g. (0.021 mole) of yellow oil. The latter material is dissolved in methanol, treated with 0.021 mole (1.9 g.) of oxalic acid in methanol and evaporated to dryness in vacuo. The residue is triturated with ether to give a white solid. The solid is recrystallized from methanol with charcoal, m.p. 198°–199°.

EXAMPLE 5A 5-(3-Ethoxypropyl)-3-iodo-5H-dibenzo[a,d]cyclohepten-5-ol

3-Ethoxypropyl bromide (7.5 g., 0.045 mole) is converted to the Grignard reagent using standard procedures (see above). To this solution (ca 60 ml.), stirred in an ice bath, is added dropwise a solution of 10 g. (0.030 mole) of 3-iodo-5H-dibenzo[a,d]cyclohepten-5-one in 30 ml. of dry THF. The mixture is stirred for 5 minutes and concentrated in vacuo. The residue is treated with saturated ammonium chloride solution and extracted three times with ether. The ether layer is washed once with water, dried over sodium sulfate, and evaporated in vacuo to an orange solid, m.p. 95°–105° (12.0 g., 95%).

EXAMPLE 5B 5-(3-Ethoxypropyl)-3-iodo-5H-dibenzo[a,d]cycloheptene 5-(3-Ethoxypropyl)-3-iodo-5H-dibenzo[a,d]cyclohepten-5-ol (8.35 g., 0.020 mole) is mixed thoroughly with 7.6 g. (0.20 mole) of sodium borohydride and the mixture added carefully in portions to 130 ml. of trifluoroacetic acid stirred vigorously in an ice bath. A moderate stream of nitrogen is passed over the mixture throughout the addition, which is carried out in an efficient fume hood, and upon completion of the addition, the mixture is stirred for 15 minutes and concentrated in vacuo. The residue is treated with ice water, and the resulting gum separated by decantation. This residue is dissolved in toluene, extracted three times with 1 N NaOH, washed once with water, and dried over sodium sulfate. The solution is evaporated in vacuo to give the title compound as an orange oil.

EXAMPLE 5C 5-(3-Iodopropyl)-3-iodo-5H-dibenzo[a,d]cycloheptene

Phosphorus pentoxide (1.28 g.) and concentrated (85%) phosphoric acid (2.7 ml.) are mixed well and cooled to room temperature. Potassium iodide (6.6 g., 0.04 mole), finely powdered, and 5-(3-ethoxypropyl)-3-iodo-5H-dibenzo[a,d]cycloheptene (4.0 g., 0.01 mole) are added and the mixture stirred and heated in an oil bath at 110° for 16 hours.

The cooled mixture is treated with 15 ml. of water and extracted three times with ether. The combined ether layers are washed with water, dried over sodium sulfate, and evaporated in vacuo to provide the title compound (5.1 g., ca 100%) as a brown oil.

EXAMPLE 5D

N-Cyclopropyl-3-(3-iodo-5H-dibenzo[a,d]cyclohepten-5-yl)propylamine hydrogen oxalate 5-(3-Iodopropyl)-3-iodo-5H-dibenzo[a,d]cycloheptene (2.1 g., 0.0043 mole) is combined with 1.42 g. (0.025 mole) of cyclopropylamine and the solution stirred at room temperature for 18 hours. The mixture is concentrated in vacuo, suspended in methylene chloride, and washed once with 0.5 N NaOH and three times with water. The methylene chloride solution is dried over sodium sulfate, and evaporated in vacuo to a brown oil which is chromatographed on 45 g. of silica gel GF (eluted with chloroform, 2%, 5%, and 8% methanol/chloroform). the product fraction is evaporated to a yellow oil.

the oil, dissolved in methanol, is treated with an equimolar quantity of oxalic acid in methanol, and the solution is evaporated in vacuo. The residue, triturated with ether, provides 1.68 g. (0.003 mole) of the title compound. Recrystallization from methanol/acetonitrile gives material melting 167°–168.5°.

EXAMPLE 6

N-t-Butyl-3-(3-iodo-5H-dibenzo[a,d]cyclohepten-5-yl)propylamine oxalate 5-(3-Iodopropyl)-3-iodo-5H-dibenzo[a,d]cycloheptene (2.1 g., 0.0043 mole) is dissolved in 1.82 g. (0.025 mole) of t-butylamine and the solution stirred 18 hours at room temperature. The suspension is evaporated in vacuo, treated with 0.5 N NaOH, and extracted three times with methylene chloride. The methylene chloride fractions are combined, washed three times with water, dried over sodium sulfate, and evaporated in vacuo. The residue is chromatographed on 45 g. of silica gel GF (eluted with chloroform and 2%, 5%, and 8% methanol in chloroform). The product fraction is evaporated in vacuo. The resulting oil is dissolved in methanol, treated with one equivalent (one half mole) of oxalic acid in methanol, and evaporated in vacuo. The residue, triturated with ether, provides 1.25 g. of pale yellow powder. This solid, recrystallized from methanol/acetonitrile, melts at 217.5°–218.5°.

EXAMPLE 7

Reduction of Other Dibenzocycloheptene-5-ols

The procedure of Example 1D is repeated except that the 0.020 mole of 3-amino-5-(3-ethoxypropyl)-7-iodo-5H-dibenzo[a,d]cyclohepten-5-ol is replaced with 5-(3-

N,N-dimethylaminopropyl)-5H-dibenzo[a,d]cyclohepten-5-ol with resultant production in high yield of the corresponding N,N-dimethyl-3-(5H-dibenzo[a,d]cyclohepten-5-yl)-propylamine.

The procedure of Example 1D is repeated except that the 0.020 mole of 3-amino-5-(3-ethoxypropyl)-7-iodo-5H-dibenzo[a,d]cyclohepten-5-ol is replaced with 3-bromo-5-(3-N,N-dimethylaminopropyl)-5H-dibenzo[a,d]cyclohepten-5-ol with resultant production in high yield of the corresponding N,N-dimethyl-3-(3-bromo-5H-dibenzo[a,d]cyclohepten-5-yl)-propylamine.

The procedure of Example 1D is repeated except that the 0.020 mole of 3-amino-5-(3-ethoxypropyl)-7-iodo-5H-dibenzo[a,d]cyclohepten-5-ol is replaced with 3-amino-5-(3-N,N-dimethylaminopropyl)-5H-dibenzo[a,d]cycloheptene-5-ol with resultant production in high yield of the corresponding N,N-dimethyl-3-(3-amino-5H-dibenzo[a,d]cyclohepten-5-yl)propylamine.

The procedure of Example 1D is repeated except that the 0.020 mole of 3-amino-5-(3-ethoxypropyl)-7-iodo-5H-dibenzo[a,d]cyclohepten-5-ol is replaced with 3-bromo-5-(3-ethoxypropyl)-5H-dibenzo[a,d]cyclohepten-5-ol with resultant production in high yield of the corresponding 3-bromo-5-(3-ethoxypropyl)-5H-dibenzo[a,d]cycloheptene.

What is claimed is:

1. A process for the reductive dehydroxylation of 5-(aminoalkyl or alkoxyalkyl)-5-hydroxy-5H-dibenzo[a,d]cycloheptene compound having one or more substituents or centers of unsaturation susceptible to catalytic hydrogenation which comprises contacting said 5H-dibenzo[a,d]cycloheptene compound with an alkali metal or ammonium borohydride in trifluoroacetic acid to produce the corresponding 5-(aminoalkyl or alkoxyalkyl)-5H-dibenzo[a,d]cycloheptene compound.

2. A process according to claim 1 wherein the 5H-dibenzo[a,d]cycloheptene starting material is a compound of the formula

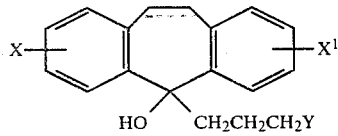

wherein
the dotted line is an optional added bond;
Y is a loweralkoxy substituent or an amino substituent which may be mono- or dialkylated, e.g.,

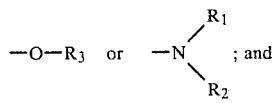
; and

X and X² are similar or dissimilar and are selected from hydrogen, an alkyl group having up to 6 carbon atoms, an alkenyl group having up to 6 carbon atoms, a perfluoroalkyl group having up to 4 carbon atoms, a phenyl or a substituted phenyl radical, an amino, an alkylamino group having up to 4 carbon atoms, a dialkylamino group having up to 8 carbon atoms, an alkylsulfonylamino group having up to 4 carbon atoms, halogen (fluorine, chlorine, bromine, or iodine), hydroxyl, an alkoxyl group having up to 4 carbon atoms, a perfluoroalkoxyl group having up to 4 carbon atoms, an alkylmercapto group having up to 4 carbon atonms, a perfluoroalkylmercapto group having up to 4 carbon atoms, an alkylsulfonyl group having up to 4 carbon atoms, a perfluoroalkylsulfonyl group having up to 4 carbon atoms, sulfamoyl, an alkylsulfamoyl group having up to 4 carbon atoms, or a dialkylsulfamoyl group having up to 8 carbon atoms.

3. A process according to claim 2 wherein the 5H-dibenzo[a,d]cycloheptene starting material is a compound of the formula:

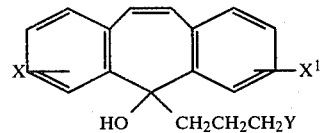

4. A process according to claim 3 wherein the borohydride compound used is sodium borohydride.

5. A process according to claim 4 wherein the 5H-dibenzo[a,d]cycloheptene starting material is 3-amino-5-(3-ethoxypropyl)-7-iodo-5H-dibenzo[a,d]cyclohepten-5-ol and the product of the reaction is 3-amino-5-(3-ethoxypropyl)-7-iodo-5H-dibenzo[a,d]cycloheptene.

6. A process according to claim 4 wherein the 5H-dibenzo[a,d]cycloheptene starting material is 3-amino-5-(3-ethoxypropyl)-5H-dibenzo[a,d]cyclohepten-5-ol and the product of the reaction is 3-amino-5-(3-ethoxypropyl)-5H-dibenzo[a,d]cycloheptene.

7. A process according to claim 4 wherein the 5H-dibenzo[a,d]cycloheptene starting material is 3,7-diiodo-5-(3-N,N-dimethylaminopropyl)-5H-dibenzo[a,d]cyclohepten-5-ol and the product of the reaction is N,N-dimethyl-3-(3,7-diiodo-5H-dibenzo[a,d]cyclohepten-5-yl)propylamine.

8. A process according to claim 4 wherein the 5H-dibenzo[a,d]cycloheptene starting material is 3-iodo-5-(3-N,N-dimethylaminopropyl)-5H-dibenzo[a,d]cyclohepten-5-ol and the product of the reaction is N,N-dimethyl-3-(3-iodo-5H-dibenzo[a,d]cyclohepten-5-yl)propylamine.

9. A process according to claim 4 wherein the 5H-dibenzo[a,d]cycloheptene starting material is 5-(3-ethoxypropyl)-3-iodo-5H-dibenzo[a,d]cyclohepten-5-ol and the product of the reaction is 5-(3-ethoxypropyl)-3-iodo-5H-dibenzo[a,d]cycloheptene.

10. A process according to claim 4 wherein the 5H-dibenzo[a,d]cycloheptene starting material is 5-(3-N,N-dimethylaminopropyl)-5H-dibenzo[a,d]cyclohepten-5-ol and the product of the reaction is N,N-dimethyl-3-(5H-dibenzo[a,d]cyclohepten-5-yl)propylamine.

11. A process according to claim 4 wherein the 5H-dibenzo[a,d]cycloheptene starting material is 3-bromo-5-(3-N,N-dimethylaminopropyl)-5H-dibenzo[a,d]cyclohepten-5-ol and the product of the reaction is N,N-dimethylamino-3(3-bromo-5H-dibenzo[a,d]cyclohepten-5-yl)propylamine.

12. A process according to claim 4 wherein the 5H-dibenzo[a,d]cycloheptene starting material is 3-amino-5-(3-N,N-dimethylaminopropyl)-5H-dibenzo[a,d]cycloheptene and the product of the reaction is N,N-dimethyl-3(3-amino-5H-dibenzo[a,d]cyclohepten-5-yl)propylamine.

13. A process according to claim 4 wherein the 5H-dibenzo[a,d]cycloheptene starting material is 3-bromo-5-(3-ethoxypropyl)-5H-dibenzo[a,d]cyclohepten-5-ol and the product of the reaction of 3-bromo-5-(3-ethoxypropyl)-5H-dibenzo[a,d]cycloheptene.

* * * * *